US006635075B2

(12) United States Patent
Li et al.

(10) Patent No.: US 6,635,075 B2
(45) Date of Patent: *Oct. 21, 2003

(54) METHOD AND APPARATUS FOR TREATMENT OF SKIN ITCH AND DISEASE

(76) Inventors: Huan-Chen Li, 31 James St., Malden, MA (US) 02148; Xiao-Guang Wang, 31 James St., Malden, MA (US) 02148

( * ) Notice: Subject to any disclaimer, the term of this patent is extended or adjusted under 35 U.S.C. 154(b) by 0 days.

This patent is subject to a terminal disclaimer.

(21) Appl. No.: 09/758,706

(22) Filed: Jan. 11, 2001

(65) Prior Publication Data

US 2001/0008974 A1 Jul. 19, 2001

Related U.S. Application Data

(63) Continuation-in-part of application No. 09/502,992, filed on Feb. 11, 2000, which is a continuation-in-part of application No. 09/183,639, filed on Oct. 30, 1998, now abandoned, and a continuation-in-part of application No. 08/698,323, filed on Aug. 14, 1996, now abandoned, and a continuation-in-part of application No. 08/601,196, filed on Feb. 14, 1996, now abandoned, and a continuation-in-part of application No. 08/254,273, filed on Jun. 6, 1994, now abandoned, and a continuation-in-part of application No. 08/157,572, filed on Nov. 24, 1993, now abandoned, and a continuation-in-part of application No. 08/131,987, filed on Oct. 4, 1993, now abandoned.

(51) Int. Cl.$^7$ .................................................. A61F 5/00
(52) U.S. Cl. ....................................................... 607/96
(58) Field of Search ......................... 607/96, 108–112, 607/114

(56) References Cited

U.S. PATENT DOCUMENTS

| | | | | | |
|---|---|---|---|---|---|
| 4,090,517 A | * | 5/1978 | Takenaka | ...................... | 607/96 |
| 4,657,531 A | * | 4/1987 | Choi | ............................ | 607/96 |
| 4,763,657 A | * | 8/1988 | Chen et al. | .................... | 607/96 |
| 4,944,297 A | * | 7/1990 | Ratkoff et al. | ................. | 607/96 |
| 5,327,886 A | * | 7/1994 | Chiu | ............................ | 607/96 |
| 6,245,093 B1 | * | 6/2001 | Li et al. | ....................... | 607/0.6 |

* cited by examiner

Primary Examiner—Robert L. Nasser
(74) Attorney, Agent, or Firm—Mark P. White

(57) ABSTRACT

An apparatus and method that is effective for the treatment of skin itch and skin rash is disclosed. The apparatus is contained within a body which can be easily manipulated with one hand, and which is powered by a self-contained battery. Also contained within the body is a heating means, controlled by a thermostat, a temperature selector, and means to warn the user when the desired temperature is reached. In addition the apparatus includes means to apply the heat in a cyclical manner, in which the heat is repeatedly applied and removed, with a cycle time and pulse width in which is controlled by user by means of a control located on the body heater and some other elements that can ensure only the effective temperature is used. The method, which is related to the apparatus as its governing principle, includes the application of heat at a precise, controlled temperature, for a specific period of time, t the skin at the location of the itch or rash. The temperature used depends upon the nature of skin discomfort, but is generally in the range between 49–62° C. In addition, the method includes a pulsating application of heat to the skin area, in which the heat is alternately applied and removed at a rate of approximately 1 second, with a total application time of between 10 and 30 seconds.

14 Claims, 8 Drawing Sheets

METHOD AND APPARATUS FOR TREATMENT OF SKIN ITCH AND DISEASE

PROSECUTION HISTORY

This application is a continuation-in-part of the application Ser. No. 09/502,992 filed on Feb. 11, 2000, which derives from a chain of continuations-in-part including Ser. Nos. filed on 09/183,639 now abandoned filed on Oct. 30, 1998, 08/698,323 now abandoned filed on Aug. 14, 1996, 08/254,273 now abandoned filed Jun. 6, 1994, 08/131,987 now abandoned filed Oct. 4, 1993, 08/601,196 now abandoned filed Feb. 14, 1996, and 08/157,572 now abandoned filed Nov. 24, 1993, and original application Ser. No. 08/131,987 filed Oct. 4, 1993, the earliest filing date of this application is hereby claimed.

FIELD OF THE INVENTION

This invention relates to methods and devices for the treatment of inches, rashes, and skin-diseases, and particularly to such methods and devices which effect such treatments by the application of heat at specific temperatures and for specific periods of time.

BACKGROUND OF THE INVENTION

Doctors know that UV light relieves psoriasis and eczema, but how? Use activated vitamin D did not give the same effect. It is now known that UV activates a group of genes called stress-genes, which produce stress proteins. These proteins are responsible for keeping the skin healthy and beautiful, and effectively clear up skin problems. Since UV can also cause DNA damage and skin-cancer, it is not the ideal means to activate stress-genes. Many other forms of energy have been found to be not only more powerful than UV in activating stress-genes, but also more effective at clearing up skin problems.

Since heat is the safest energy, it does not cause DNA damage, or skin-cancer, and it is the most effect one in activate stress genes. Also, since the heat destroys toxins below the surface of the skin and shows the best results in clearing up skin-problems, the present invention is intended for the treatment of skin itch, skin rash, and related skin diseases by means of the controlled application of heat.

The use heat in the treatment of skin diseases has been known for a long time. folk remedies using heat exist in many different cultures, and the origins of these remedies are often obscure.

However, the use of heat in the treatment of skin itch and rash is different from such treatment for other skin problems. An article in the British Journal of Dermatology 122(4): 501–12, 1990, by Benee A. Glover, Cynthia S. Bailey, Kim E. Barrett, S. I. Wasserman and Irma Gifli, of the Division of Dermatology and Allergy Department of Medicine, University of CA, San Diego School of Medicine, San Diego, Calif. entitled: *Histamine release from rodent and human mast cells induced by protoporphyrin and ultraviolet light: studies of the mechanism of mast-cell activation in erythropoietic protoporphyria, deals with just this issue.* In a study reported therein, it was found that heating or prolonged heating at temperatures lower than 45° C. exacerbates skin itch and rash, but does not have any detrimental effect on most other skin problems. Those temperature ranges found effective against itch and rash are generally in excess of 49° C., Sufficiently hot to result in pain if applied to the skin for more than 3 seconds.

Furthermore, for treating itch and rash the temperature must be maintained at the superficial surface, that is not deeper than dermis where the mast cells are located. This must be done without burning the skin, or causing excessive discomfort. The mast cells must be inactivated, but the inner part tissues such as blood vessels must be maintained at a safe temperature, thus avoiding edema and pain. This is so whether or not the inactivation of mast cells is the sole mechanism for stopping itch. There is some variation of the best effective temperature for treating itch and rash, depending on factors which are discussed below.

The inventor has been found that different types of itches and rashes require different treatment temperatures. These best effective temperatures depend, inter alia, on whether the patient being treated is a child or an adult and women or men. All of the treatment temperatures require, however, are within a range of about 10° C. It has been found that the use of these best effective temperatures, to within a tolerance of plus or minus one-half, effectively avoids side effects, such as edema and rebound of itch. And, for most people, temperatures below 49° C. must be avoid, as they worsen itch and rash, rather than providing relief. All of the effective temperatures against itch have been found to be above 49° C. Temperatures of 49±0.5° C. have been fond optimum for children, as have temperatures of 52±0.5° C. C for adults and 47° C. is for toddlers and some temperature sensitive women, in the case of itch.

Different parts of the body have also been found to have different best effective temperatures. For example, 50° C. is the best temperature for a child or an adult face, 52° C. for adult body and arm skin, and 54° C. for adult leg skin. If 50° C. is used for adult leg skin that is thicker than the face skin, the itch will not be stopped and side effects, such as edema and rebound of itch, may result. Furthermore, best effective temperature is also dependent upon the rate at which the skin is heated, and for that reason best effective temperature may change with changed in the material actually in contact with the skin. The above temperatures are for a planar steel heating surface.

New versions of the device are in development which will allow regulation of the temperature to take into account personal variations of the best effective temperature.

Experimental results, as well as the report of Glover, et al., Id., make it clear that the heating time of the skin should be as short as possible, while still receiving the benefit required. Thus the direct contact of the heating element to the skin provides the most direct method to effect an optimum treatment of this nature. This direct contact is accomplished in the present invention by a circular metal heat transfer surface of approximately one inch diameter. The direct contact also provides advantage in controlling the speed to heat up the skin. some materials can control the amount of heat to pass to the skin in a timely manner. They will be used as the skin heater or be put on the surface of the skin-heater so to heat the skin to the desired temperature in an desired time. This will avoid the pain and effectively clear up the itch. The reason for this is because if the skin is heated up to fast, it will get pain, if too slow, it will worsen the itch.

At present, there exist a number of commercially available devices which apply heat to the skin for therapeutic purposes. However, none of these is effective against skin itch and rash, because none of them accurately and precisely apply the required temperatures for treating itch and rash. For instance, U.S. Pat. No. 4,944,297 (Ratkoff) describes a device which is used to heat the skin, and it further contains a reflector to direct the radiation from the heating element to the skin. Such an arrangement is incapable of the precision in controlling and maintaining temperature, required of the current invention.

Other apparatuses that are already known to heat the skin for therapeutic purposes are as described, for example, in the documents of U.S. Pat. Nos. 4,763,657 (Chen); 4,657,531 (choi); and 4,907,589 (Cosman). None of these have provisions to precisely control and maintain temperature, as required of the current invention.

Without a precise temperature control, measured at the surface of the skin, the user, to avoid pain, will always chose a temperature lower that the effective temperature, which will often just worsen the itch, rather than curing it.

Other old methods of heat treatment for skin ailments include the use of scalding water to heat the skin to stop itch. This method obviously can not be done with the amount of control required to effect the best effective temperature, or with control of the time of application. For these reasons, this method has been abandoned.

As shown in the following results, this invention is different from the above treatments. it clears up skin problems in about 2 months and eliminates itching within one minute. The invention is called ItchStopper in the following results.

Our clinical trial results on Psoriasis (two-month test,).

| Treatment | Itch erased in 1 minute | psoriasis complete remission | psoriasis partial remission |
|---|---|---|---|
| ItchStopper | 100% patients | 68% patients | 17% patients |
| Ultrasound | 7% patients | 54% patients | 28% patients |
| Cream | 0% patients | 0% patients | 11% patients |

The heat may also destroy the toxin of poison ivy: When the poison ivy was treated with the Itch Stopper for about 3 minutes then applied to patients, it failed to cause any poison-ivy symptoms in all patients tested, indicating the Electronic Itch Stopper may destroy poison ivy.

The Electronic Itch Stopper worked on every poison-ivy patient tested.

| Treatment | Success*/Number (itch erased) | Itch-stop starting time | itch-stop lasting-time (hours) |
|---|---|---|---|
| Itch-Stopper | 200/200 | 21.08 ± 6.94 # seconds | 17.04 ± 5.19 |
| Cortaid | 0/20 | 51.21 ± 8.31 minutes | 3.00 ± 0.93 |

*Success means itch was stopped within one minutes
$P < 0.001$, difference statistically significant as compared to the control Effect on poison-ivy-erythema size: Visible erythema size decreases were observed in 30 minutes after the Electronic Itch Stopper treatment while in the control group, no changes was observed.

on poison-ivy-erythema size change after treatment (20 patients)

| treatment | Erythema size (mm$^2$) after treatment | | |
|---|---|---|---|
| | 10 minutes# | 20 minutes | 30 minutes |
| Itch-Stopper | 1331 ± 343 | 1309 ± 298.4 | 436.7 ± 144.4* |
| Cortaid | 1287 ± 252.6 | 1287 ± 252.6 | 1287 ± 252.6 |

*$P < 0.01$, difference statistically significant as compared to the control.
Before the treatment, the average-Erythema-sizes of the control and the treatment group were the same to the sizes at 10 minutes after treatment.

Electronic Itch Stopper cured about 50% stage-I-acne in just three days. Among the 103 acne patients tested, 81.2% patients got significant improvement in just three days. Most patients showed visible results in 6 hours after the treatment. The following tables shows the effect.

Electronic Itch Stopper effect on stage I acne (3 day test)

| | Acne number | Complete remission | Partial# remission | No change | worsen |
|---|---|---|---|---|---|
| Treated | 76 | 37 (49%)* | 28 (39%)* | 11 (15%)* | 0 |
| Untreated | 31 | 0 | 2 (6%) | 26 (84%) | 3 (10%) |

*$P < 0.01$, effect statistically significant as compared to the control
measurable and visible remission.

Every acne has its early stage. If patients treat all their acne in the early stage, their acne problem will be eliminated.

Electronic Itch Stopper success rate on itch dues to herpes, eczema, ulticaria, and dermatitis is about 98.4%.

The apparatus disclosed in detail below is both practical and economical to use. In addition to its preferred forms it may be made in a variety of sizes and shapes.

The device includes easy-to-understanding instructions which specify the best effective temperature for a variety of skin conditions, skin types, and ages. A light indicator located on the body of the invention flashes when the heater reaches the predetermined temperature commanded by the temperature selector, and the user is instructed not to apply the heater until this indicator flashes. In alternate embodiments, a sonic signal is used t indicate that the devices has reached its operating temperature.

A further alternative embodiment includes a heating surface which repetitively retracts and extends. This automatic intermittent application of the heater is especially important when higher temperatures are required for the treatment, since higher temperature require shorter application times, repeated at short intervals.

Because the effective temperature against itch is so high as to be intolerable if applied for longer than 3 seconds, means are provided to heat the skin to the effective temperature range, such as 52° C., for about 2 seconds and then let it cool down to a tolerable temperature, such as 47° C., for about half second. This process is repeated for between one to ten minutes in order to cure skin diseases.

SUMMARY OF THE INVENTION

It is an object of the present invention to provide an apparatus effective against skin diseases and itch. It is a further object of this invention to provide such an apparatus which is simple, inexpensive, and portable.

According to one aspect of the current the apparatus, operating by means of the controlled application of heat, comprises heating means providing a specific best effective temperature, control means to control the heater temperature in about ±1° C. A more complicated one comprises temperature selection means within the range of 46 to 56° C., means to accurately detect heater temperature, control means to regulate the temperature in concert with said detection means to within plus or minus one-half degree centigrade, and heating means controlled by said control means. The heating means are capable of raising the skin to the selected temperature within approximately ten seconds and maintaining it at that temperature. All of these are contained within a housing comprising a contact end, with the heating means positioned in the contact end. The temperature selection and detection means are also contained within the housing and are accessible to the user.

According to a second aspect of the invention, the apparatus further comprises a substantially planar heat transfer surface located at the contact end, heated by said heating means. This surface is substantially circular, with a diameter of at least one-half inch. Material that allow a desired amount of heat to pass to the skin in a desired time may be used as the planar or be put on the surface of it.

According to a third aspect of the invention, the apparatus further comprises signaling means to indicate that the user's skin is at the selected temperature, as well as means to select one of a multiplicity of temperatures, each such temperature comprising a best effective temperature for a particular treatment, and comprising means to control skin temperature to within one-half degree centigrade.

According to a forth aspect of the invention, the heating means further comprises a slideably moveable heating surface positioned within the contact end, said heating surface having an extended position in which the surface is in contact with the skin of the user and a retracted position out of contact with the skin. Also included are means to position the surface at either position, and selection means to control said motion.

According to a fifth aspect of the invention, the positioning and selection means provide a periodic motion of the heating surface, and the selection means provides control of frequency and duty cycle of said motion.

According to a sixth aspect of the invention, the apparatus further comprises means to select one or more additional temperatures, so that, when cyclical operation is selected, heat will be alternately be applied first at the first selected temperature, then at the second selected temperature, and so on until all the selected temperatures have been applied in sequence, then at the selected temperature, and repeating indefinitely.

According to a seventh aspect of the invention, the apparatus further comprises a grid at the contact end, said grip having a multiplicity of apertures. The heat transfer surface contains a multiplicity of protrusions which extend through the grid apertures when the surface is in extended position.

BRIEF DESCRIPTION OF THE DRAWINGS

These, and further features of the invention, may be better understood with reference to the accompanying specification and drawings depicting the preferred embodiment, in which.

PREFERRED EMBODIMENTS

A number of preferred embodiments of the invention are discussed in this section.

Figure 1:
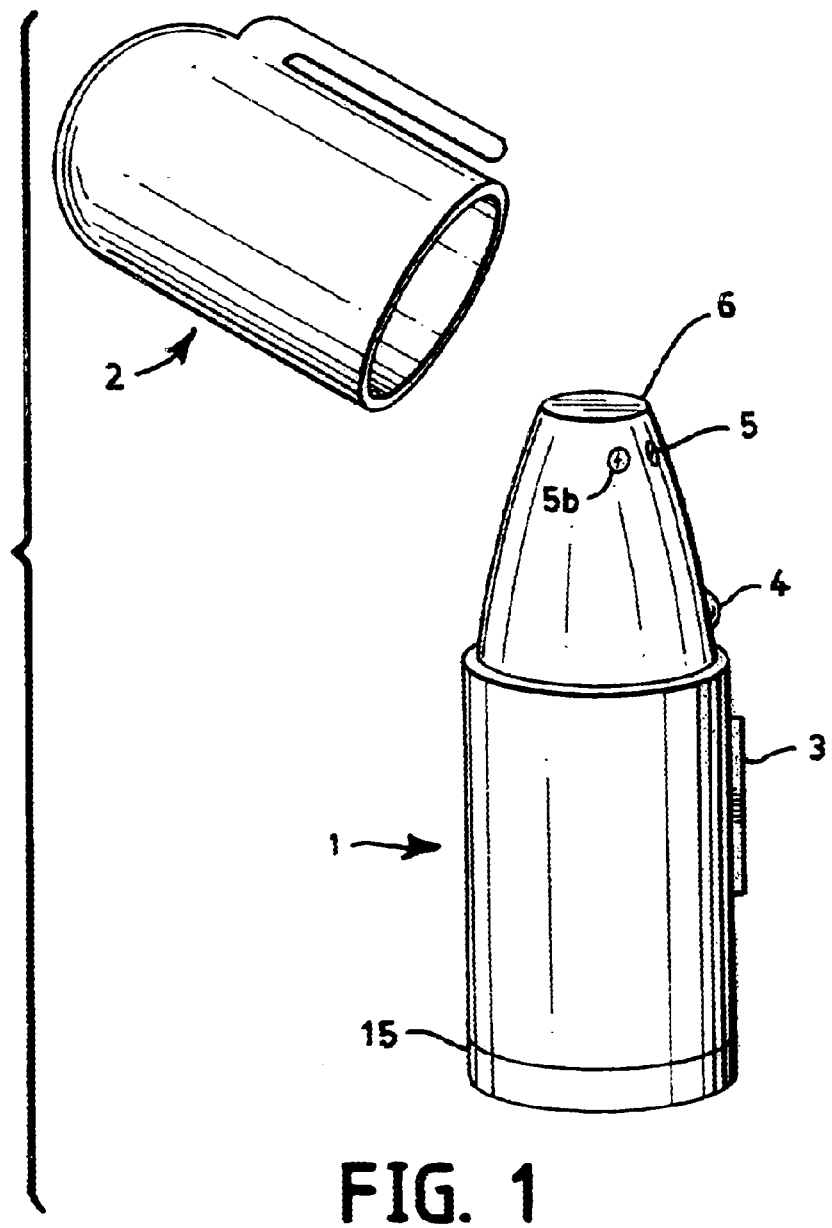
FIG. 1 is a perspective view of the present invention in its first preferred embodiment

The first preferred embodiment of the apparatus may be understood by referring to FIG. 1, showing the invention is in the form of a hand-held apparatus with self-contained power supply by means of commercially-available batteries. The apparatus includes an optional protective cap 2 and a housing 1 which contains all the remaining components of the invention. A temperature selector 3 is located half-way up the body 1. This selector is of a rotary type which selects the best effective temperature in 1 degree-centigrade increments, to within one-half-degree centigrade. A main power switch 4, turns power on and off. Light indicator 5 illuminates when the selected temperature has been reached, and light indicator 5b illuminates when power is on. Heat is applied to the skin through the heat application surface 6. A temperature transducer, or thermostat 7, is located directly adjacent to the heat application surface, so that the temperature detected is essentially that of the user's skin during application. The batteries which serve as the power source 8 are located within lower portion of the housing. Batteries are replaced by means of a screw-on cap 15, at the bottom end of the housing.

The temperature selector 3 is used in such a manner as to enable users to directly select one best effective temperature for the heater. It provides for selection of two or more predetermined temperatures. Different versions of this embodiment are provided for different ranges of temperatures, depending upon general application.

The heat application surface may be made of a number of different materials. A heat conductive metal is one of the preferred materials, especially when used in conjunction with a magnetic-induction type heater, as is the case with the first preferred embodiment. The surface may alternatively be covered by a non-heat-conducting coating, or material, such as a thin layer of rubber, in order to reduce pain by reducing the conduction speed of the heat to the skin. Many users are more comfortable when the temperature rises gradually to the best effective temperature. Such a gradual temperature rise is found to be equally effective as a rapid rise, in regard to the curing of skin itch and rashes.

Figure 1B:
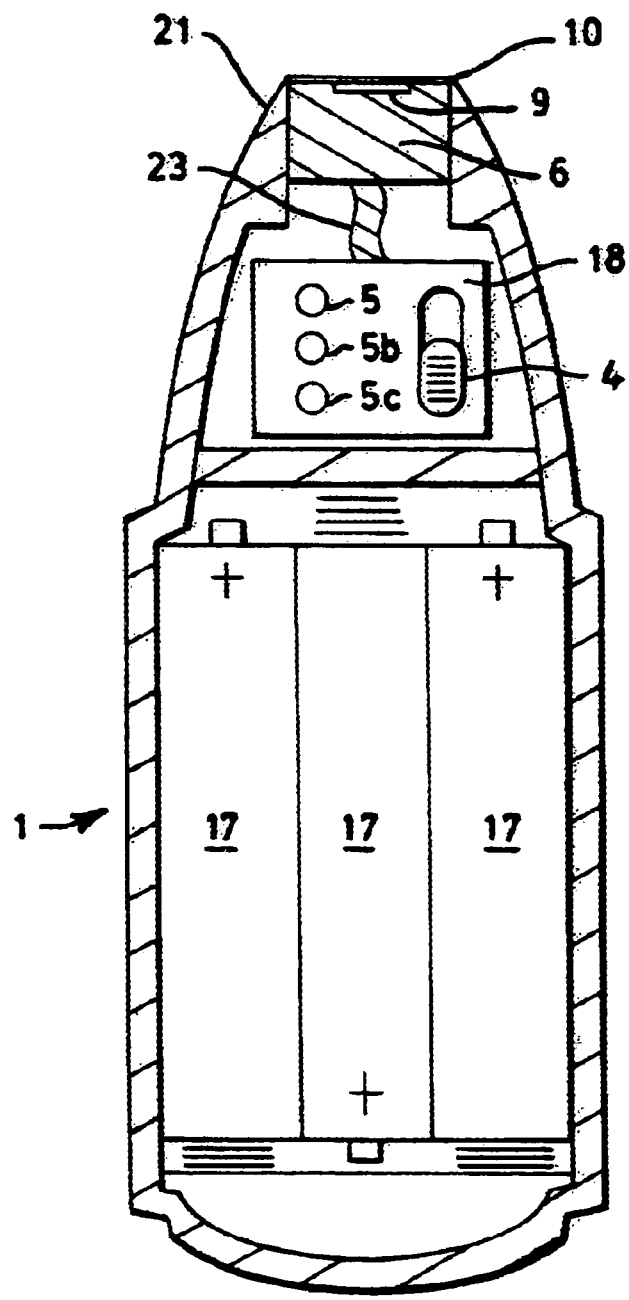
FIG. 1B is a cross-section view of the model SM version of the invention, a variation of the first preferred embodiment.

A variation of the first preferred embodiment is shown as FIG. 1b, and corresponds to a commercially-offered version of this invention, model SM, as mentioned above. In this cross-section view, the batteries are show as the commonly used "AA" cells, with three such cells 17 mounted within the housing 3 as described above. The electronics used to control the device are mounted on circuit board 18, located in the upper part of the housing as shown. In model SM, there is a third indicator light 5c, mounted on the circuit board together with indicator lights 5 and 5b. In this implementation, the indicators represent "Ready" 5, "Child 5c", and "Adult" 5b. In the implementation of FIG. 1B the switch 4 has three positions, corresponding to off, "Child", and "Adult". The Adult and Child switch positions correspond to two different temperatures, thought to be optimum for eczema and psoriasis, for children and adults, respectively. When either Child or Adult position is selected, the Ready light indicates that the apparatus has reached the selected temperature. In this embodiment, the heat application surface presents a flat, circular surface flush with the contact end of the housing, as shown in FIG. 1a. This surface has a diameter of approximately ⅜ inch.

The heating transfer surface in this embodiment is combined with the heating element itself in one integral unit. The circuit board contains control electronics which supplies current to the heating element through cable 21 when the temperature sensed is below the temperature commanded by temperature selector 3. If the temperature reaches or exceeds the temperature commanded, the current is discontinued. The control electronics provide a smooth response profile (i.e. temperature vs. time), with a minimum of overshoot, to a precision of plus or minus one-half degree centigrade.

A second commercially-available version of this invention, Model LD previously described, is very similar to this first preferred embodiment, except that Model LD has a cord allowing the device to plugged into a normal household utility outlet. The heat transfer surface in this version is metal, and presents a flat, circular plate flush with the contact end, as in Model SM. However, the diameter of the surface in Model LD is approximately one inch. This greater surface area allows application to a larger skin area, and is facilitated by the high power available from using house current as a power source.

Model LD also provides only two indicator lights, indicating "ON/OFF", and "READY".

In one of the variations of this first preferred embodiment, the selector switch allows the user to chose one of many different discrete temperatures within the range of the apparatus. This switch is used in place of the three-position switch of FIG. 1b, and is shown in FIG. 2A. The switch contains a rotor 19, with a pointer 20 to indicate which of the positions is selected. The switch has allowing the selection of one of the temperatures indicated, with one of the positions being "OFF". Only two indicator lights are used in conjunction with this variation: "ON" and "READY". Illumination of the "READY" indicator indicates that the apparatus has reached the selected temperature.

Figure 3:
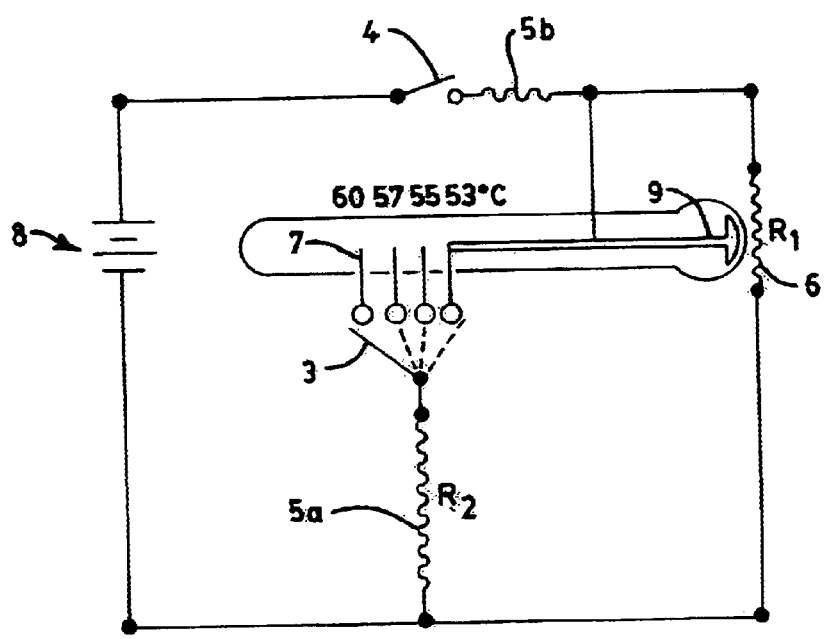
FIG. 3 is a block diagram of he electronic circuit for the temperature probe/thermostat embodiment of the apparatus.

The electronic implementation of the apparatus can take many forms. Many different methods of heating are available, and the art of heat control systems for small appliances is well developed. FIG. 3 depicts the operation of the apparatus in one implementation in the form of an electrical schematic. The power source in the form of a battery 8, is connected through switch 4 in series with indicator light 5b to the temperature transducer 9, and heater 6. The multi-position switch 3 selects one of several contacts which detect different positions along the transducer corresponding to different temperatures. When the selected temperature is reached, the transducer makes an electrical connection with the rest of the system, allowing the "READY" indicator 5a to illuminate. The temperature transducer in FIG. 3 is temperature probe 9 filled with mercury. When the heater is at lower than the selected temperature, the thermostat allows the maximum current to go through the heating element. When the heater reaches the selected temperature, the mercury will serve as a conductor to divide and therefore reduce the heater current, thereby reducing it sufficiently to maintain the selected temperature.

Figure 2:
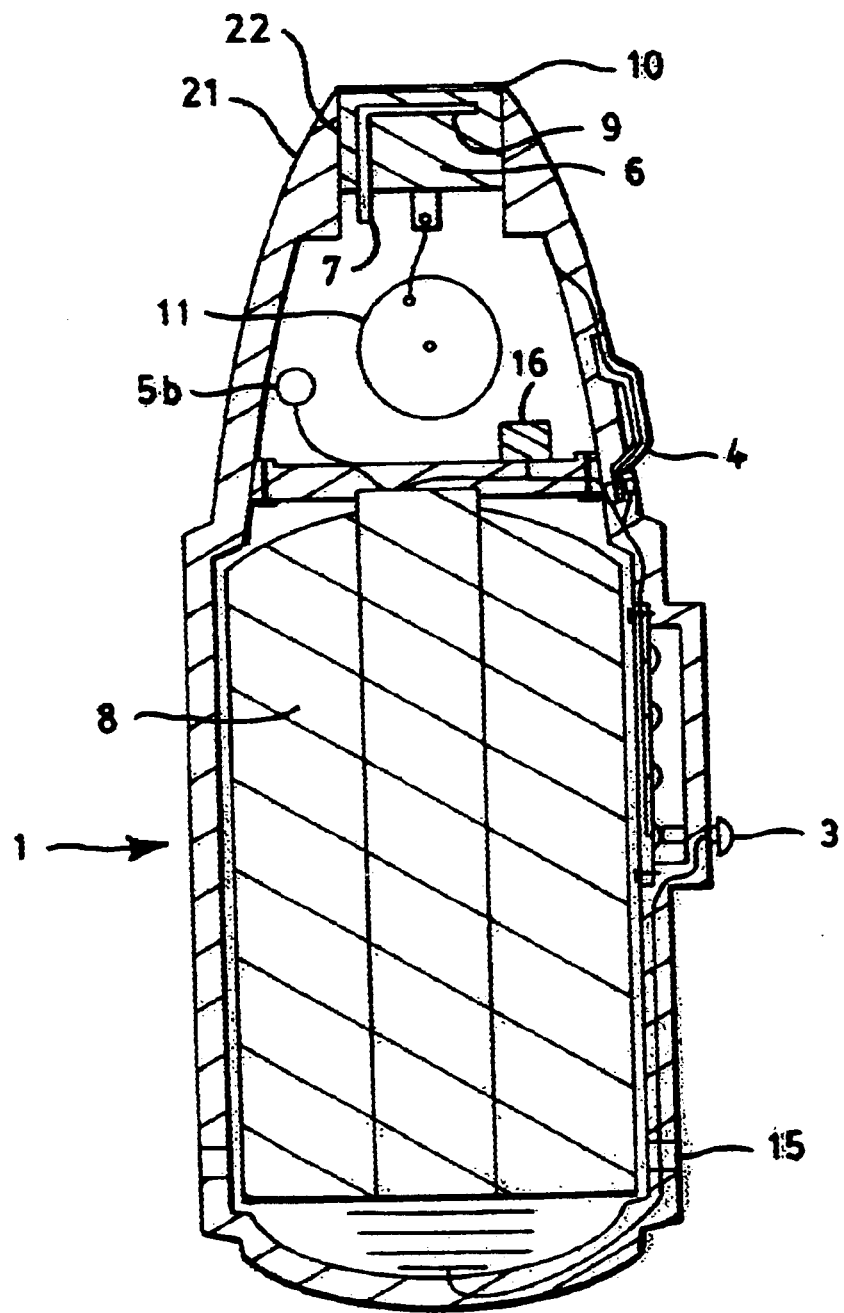
FIG. 2 is a section view of the mechanical pulsation embodiment of the invention.
Figure 2A:
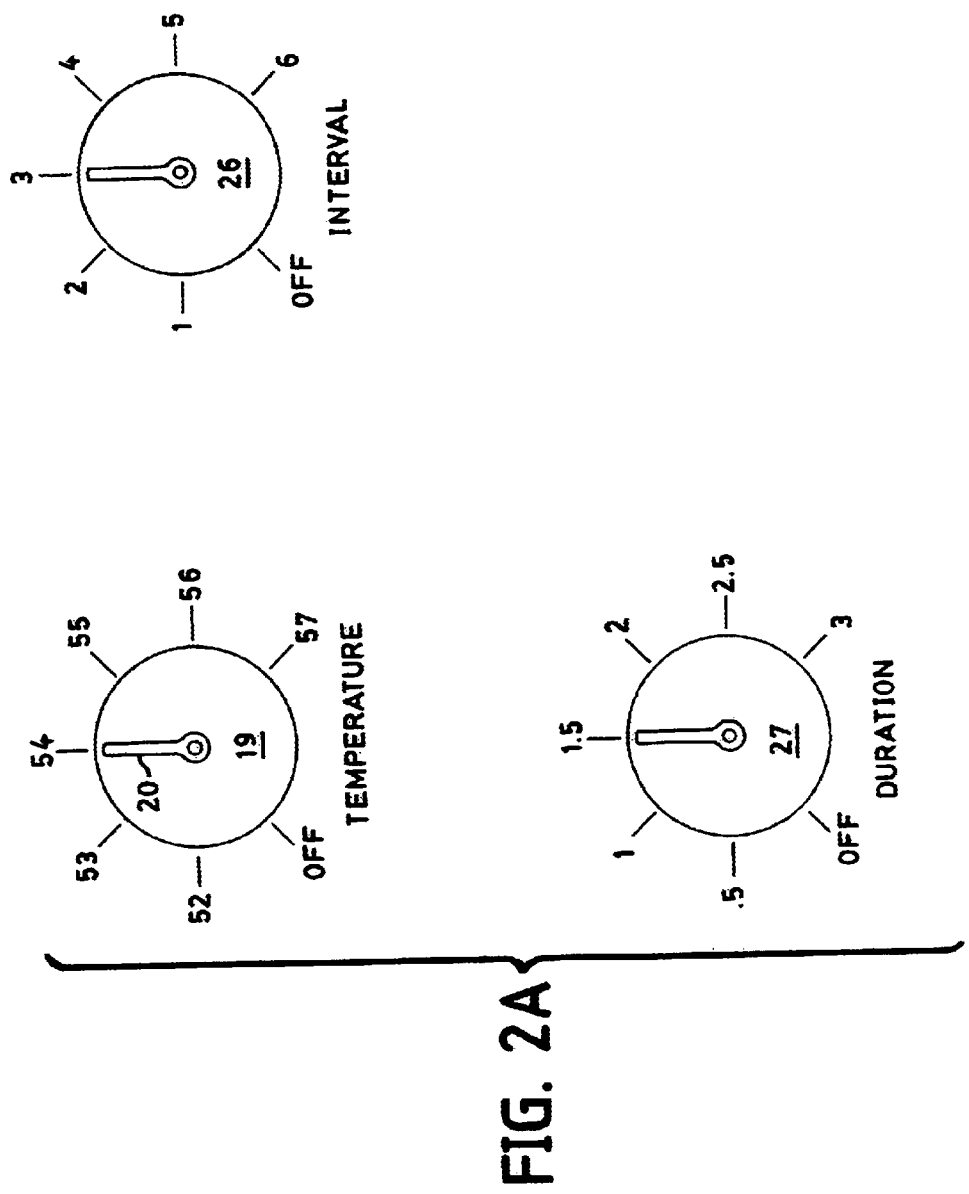
FIG. 2B is a plan view of the selector switches used to control operation of the mechanical pulsation, and indirect heating embodiments.

A second preferred embodiment of the current invention is depicted in FIG. 2. In this embodiment the heat transfer surface/heater combination is slidingly mounted in a channel 22 within the contact end of the apparatus. The heater has an extended position, in which the heater is in contact with the skin of the user, and a retracted position in which the heater is withdrawn within the channel. The heater is driven between its two positions by a positioning mechanism 11, which consists of a motor/crank combination in this embodiment. An alternative variation uses a solenoid as a positioning mechanism in place of the motor/crank actuator.

In this embodiment the temperature selection/detection control moves the heater against the skin of the user, and away from the skin in a repetitive manner, at a rate controlled by the user by means of two selector switches. One such switch controls the rate at which the heater moves against the skin, in seconds per cycle. The second switch controls the duration of the application, in seconds. The ratio of the duration of the application to the time between applications is called the "duty cycle".

It has been found that such a pulsating application of heat is better tolerated by many users than a prolonged application of heat in constant contact with the skin. Toleration varies widely from one individual to another. This embodiment allows users to regulate the duty cycle of the application to suit their individual needs.

A variation of this embodiment includes a grid 10 at the contact end of the apparatus, and in contact with the skin of the user during application. The heat application surface contains raised projections which mate with the grid, and protrude through the grid when the heater is in the extended position, so that these projections are in contact with the skin in this position. This grid provides a safety mechanism when the heating element is retracted. It also allows the temperature detector to be located in the grid itself, which is in contact with the skin, thus providing an more accurate measure of skin temperature.

Figure 4:
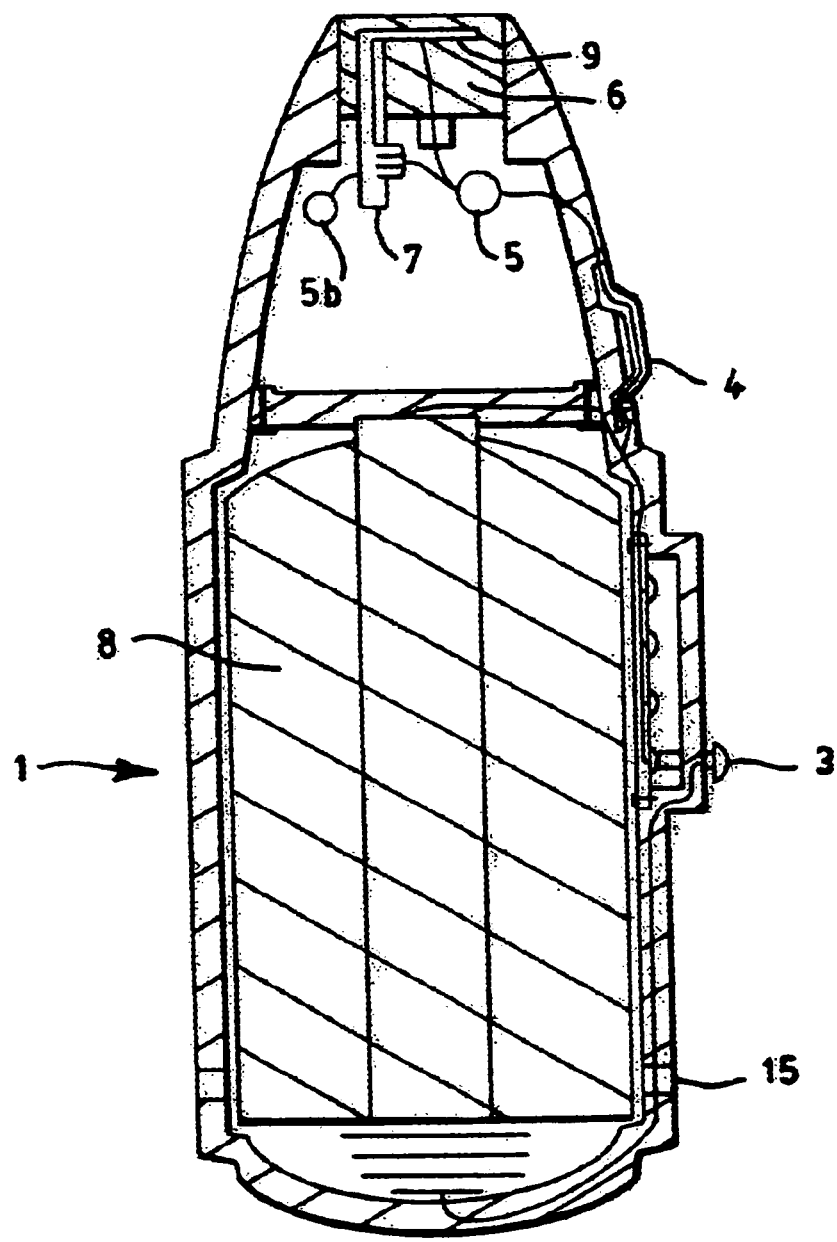
FIG. 4 is a section view of an alternate version of the temperature probe/thermostat embodiment, with alternative location of the thermostat.

The third embodiment as shown in FIG. 4 that omits the positioning means 11 and the grid 10 of the above mentioned embodiment. In this case, a light indicator 5 that will be turned on or will flash or will change color after the heater reaches the selected temperature will be include in this apparatus to replace the omitted elements 10 and 11 to ensure only said best effective temperature is used. Also in this case said heater is fixed at said contact end and said intermittent application of heat is performed manually. it would be possible to omit the light indicator 5 if a strong and stable power source, together with a good heat-transfer material for the heat transfer surface are used, providing rapid heating of the transfer surface to the desired temperature, and maintaining of that temperature.

The fourth embodiment as omits the temperature selector of the second embodiment. In this embodiment the heater is fixed at one exact best effective temperature, selected for a specific skin condition.

Figure 5:
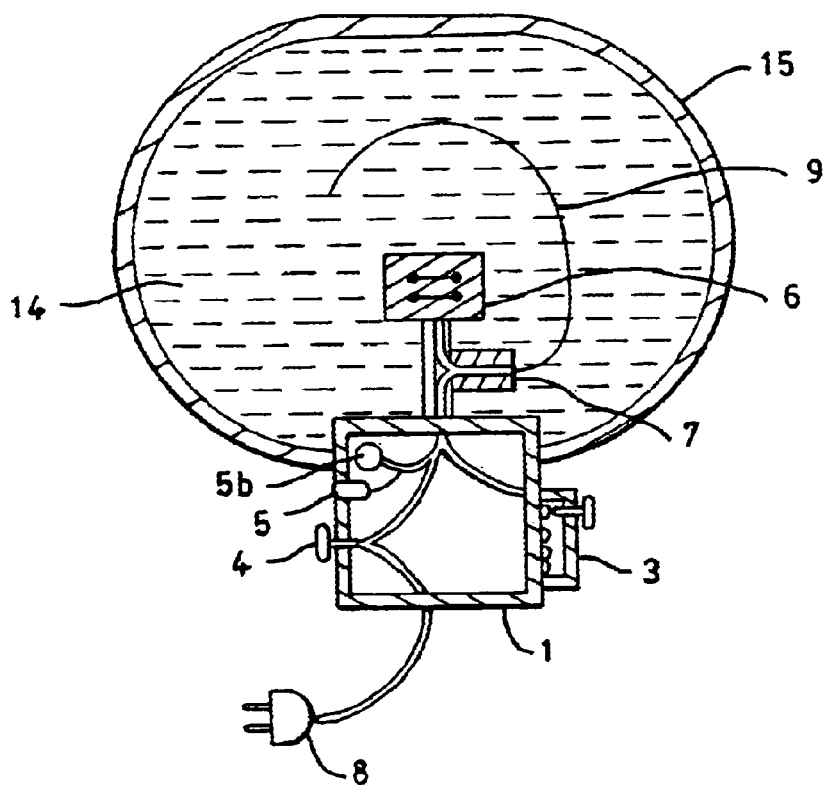
FIG. 5 is a section view of the liquid-filled heating surface embodiment.

In a fifth embodiment, as shown in FIG. 5, a heat-conducting liquid is used to maintain the temperature within the heat transfer surface which contacts the user's skin. The liquid used is preferably one with a high specific heat, such as oils of various types. The material need not be liquid at room temperature, so long as it liquefies at the best effective temperature. The advantage of this method is that the temperature and the sensing device may be located at any point within the liquid, or in proximity to the liquid, simplifying the design and manufacture of the apparatus. The high specific heat of the liquid, as well as the mobility of the molecules within the liquid, produces a uniform temperature within the body of the liquid. In contrast, metals may exhibit a thermal gradient between the area in proximity with the heater and the area in proximity with the skin, making accurate temperature control more difficult. Referring to FIG. 75, the heating element 6 is immersed in the heat transfer liquid 14, while temperature is sensed by the transducer 9, also immersed within the liquid. The liquid is contained within the heater head 25, which may be flexible or semi-rigid. A flexible material provides the advantages of allowing application of heat to a non-planar area of the skin, such as the shoulder or face. The heater head may be made of any material, such as plastic or rubber, which is soft to the touch and does not abrade the skin. the head is of a generally spherical, or ellipsoidal shape.

Still referring to FIG. 5, the remainder of this embodiment is similar to the first preferred embodiment. An external power source is used, as indicated by the utility plug 28. Indicator lights 5 and 5b are used to indicate power on, and "READY", as in previous embodiments. A multi-position selector switch 3 is used to select one of several best effective temperatures. Because of the use of an external power source, the heat transfer surface may be significantly larger than in the embodiments powered by self-contained batteries.

Figure 6:
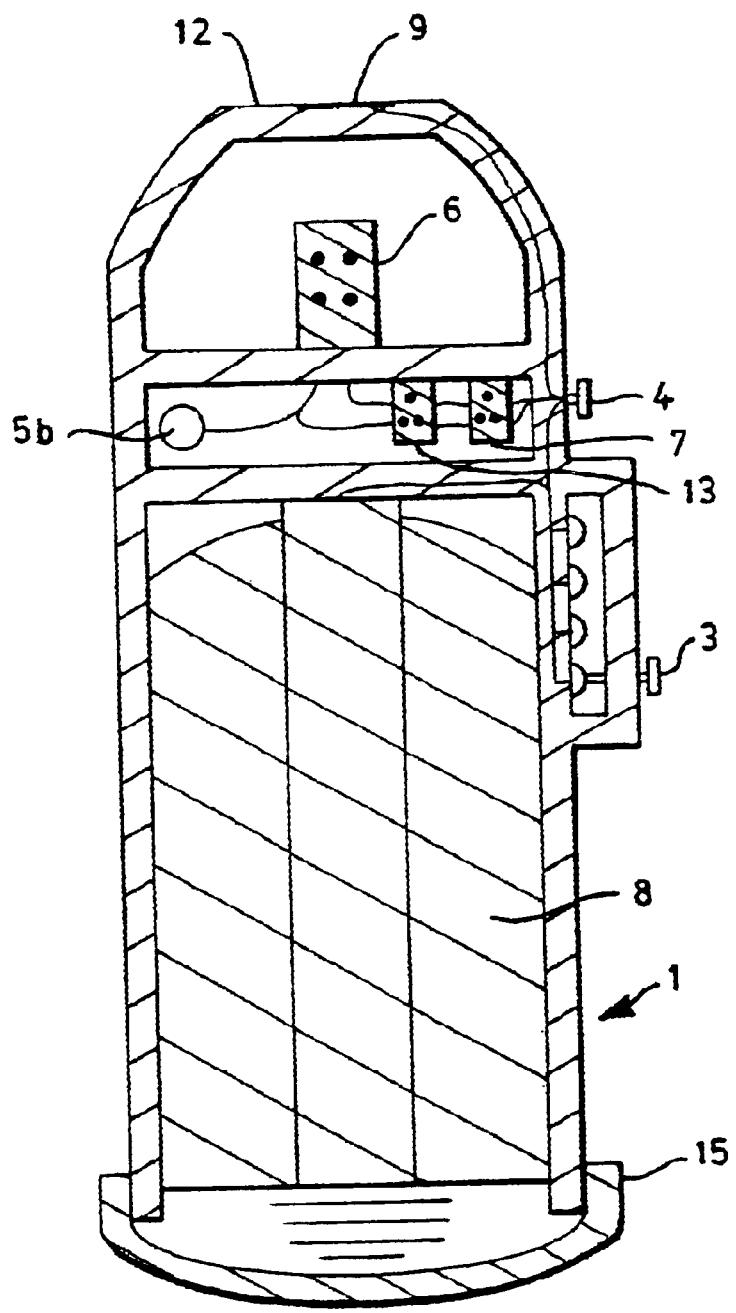
FIG. 6 is a section view of the indirect heating element embodiment.

In a sixth embodiment, as shown in FIG. 6, laser, microwave, sonic sound, and infrared radiation may also be used as a heat source for this invention. Such indirect heat sources require special means to detect heat at the surface of the skin. One recommended method is to incorporate the temperature transducer in a grid 10 located at the contact end of the apparatus, as shown in FIG. 6, which depicts a sixth preferred embodiment of the invention. In this case, the heater source will be set behind the opening at the contact end. The heater should provide a heating energy that is high enough to heat the skin to an effective temperature within about 1–2 seconds. A wall means, such as a grid, is located at this opening to prevent direct contact of the skin to the heat source 6, as will as to prevent the user from accidentally placing his fingers, or other objects, in contact with the heat source. burning. In this embodiment, the temperature transducer should be located within the wall means, in order to accurately measure the temperature at the skin of the user.

This embodiment further provides intermittent heating means without requiring a position control mechanism. Intermittent application of the heat to the skin by this method is done by switching the heat source on and off, an alternative method to that of the second preferred embodiment, which uses motor-crank mechanism, or solenoid to physically move the heat transfer surface against the skin, and periodically retract the surface. In the seventh embodiment, the apparatus includes a selector switch allowing the user to vary the duty cycle of the heat application, similar to that of the second preferred embodiment. The temperature transducer located in the wall means senses the temperature at the surface of the skin, and controls heat source so that the skin temperature reaches the temperature commanded by the temperature selector switch 3 at the times commanded by the duty cycle selectors.

A further variation of the invention involves a two chambered pouch that contains one chemical solution in one chamber and another solution in the second chamber. Upon application of pressure through twisting or pressing, the solutions will mix within a third chamber, located within the contact end, thereby heating the surface of the contact end. In another embodiment two chemical solutions would be kept separately in a bottle. Upon spraying or pouring the solution onto the skin the chemical solutions get mixed, resulting in a chemical reaction that provides heat before reaching the skin surface. Strength of the solution would be predetermined such as to provide a specific temperature of a specific range of temperature in 46° C.–62° C. The duration of heat is controlled by including in the solution alcohol or a similar chemical that will rapidly cool the surface within a brief predetermined time period. The end result is that the skin is rapidly heated to a temperature and then rapidly cooled.

An additional embodiment requires the use of a single chemical solution, located within an application vessel, to which a catalyst is added just prior to application. The catalyst may be positioned in a spray or pouring spout of the application vessel, such that the chemical solution must pass through the catalyst when the solution is either sprayed or poured. Upon spraying or pouring, the chemical solution in combination with the catalyst is mixed with oxygen in the atmosphere and a chemical reaction occurs providing heat at the skin surface. Still another embodiment would require the use of an electrical heater to heat a medical solution, volatile liquid, or gas to a specific temperature of a specific range of temperature in the range of 46–62° C., 49–62° C. or 50–69° C. The liquid may also become steam or gas in this temperature. The heated spray, heated medical solution, heated steam, or gas, is sprayed onto the skin either continuously or intermittently by manual or automatic operation. The head of the sprayer may be made small and long enough to facilitate the application of the heated spray onto the membrane inside the nose for treating itch within the nose. Thermostatic means for controlling the temperature of the spray or the liquid temperature are included in the sprayer.

The improvement method comprising heating a body heater as may be required to maintain said body heater at a substantially consistent temperature at and during the time of treatment of the skin area affected, said substantially uniform temperature being a predetermined temperature or a predetermined temperature range in ranges of about 49–69° C., 52–62° C., 52–69° C., 53–62° C., 50–62° C., 49–53° C., 54–56° C., 57–62° C., 50–70° C., or 56–62° C., and equal to a best effective temperature of a specific case; continually monitoring the temperature of the body heater to determine when and the degree of heat to be added to the body heater and to determine when adding of heat is to be discontinued; controlling the supply of power to the body heater in accordance with heat requirements determined by said temperature monitoring, and applying the body heater to the skin area that need treatment either continuously or discontinuously. Continually monitoring the temperature of the body heater within about ±0.5° C. or ±1° C. of said predetermined temperature, providing of selections of temperature, and indicating readiness to use will be included and these will help to eliminate edema and rebound of itch. The body heater can be dry and wet, such as a wet ribbon heater or a wet towel heater.

Another improvement method comprising using a body heater to heat an skin area as may be required to maintain said skin area at a substantially constant temperature at and during the time of treating said skin area affected, said substantially uniform temperature being a predetermined temperature or a narrow range of temperature in ranges of about 49–69° C., 52–62° C., 52–69° C., 53–62° C., 50–62° C., 49–53° C., 54–56° C., 57–62° C., 50–70° C., or 56–62° C., and equal to a best effective temperature of a specific case; continually monitoring the temperature of the skin area to determine when and the degree of heat to be added to the skin area and to determine when adding of heat is to be discontinued; and controlling the supply of heating power to the skin area in accordance with heat requirements either manually or automatically, or determined by said temperature monitoring. Continually monitoring the temperature of the skin area within about ±1° C. of said predetermined temperature will help to eliminate edema and rebound of itch. Heating the skin area discontinuously as monitored by a controlling means to heat the skin area to a specific narrow range of temperature in the above ranges and let the skin area to cool down to a tolerable temperature, repeating the heating and cooling until finishing the treatment, to avoid and minimizing any discomfort of heating the skin. The body heater can be dry and wet, such as a wet ribbon heater or a wet towel heater.

It will be apparent tat improvements and modifications may be made within the purview of the invention without departing from the scope of the invention defined in the appended claims.

We claim:

1. An apparatus for treating skin itch and disease, through the controlled application of heat, comprising:
   heating means for applying heat to the skin;
   temperature selection means for allowing selection of a heater temperature inside the range of 46–62 degree Celsius;
   a housing having a contact end, the heating means positioned within the contact end, and the temperature selection means located within the housing.

2. The apparatus according to claim 1 further comprising a control means to regulate the heating means temperature.

3. The apparatus in accordance with claim 2, further comprising signaling means to indicate that the heating means has reached the selected temperature.

4. The apparatus in accordance with claim 3, further comprising means to select one of a multiplicity of temperatures, each such temperature comprising a best effective temperature for a particular treatment, and comprising means to control skin temperature to within one-half degree centigrade after the selected temperature is reached.

5. The apparatus according to claim 1, wherein the heating means further composes:
   a slideably moveable heating surface positioned within the contact end, said heating surface having an extended position in which the surface is in contact with the skin of the user and a retracted position out of contact with the skin, further comprising means to position the surface at either position; and selection means to control said motion.

6. The apparatus according to claim 5, wherein said positioning and selection means provide a periodic motion of the heating surface, and wherein the selection means provides control of frequency and duty cycle of said motion.

7. The apparatus in accordance with claim 6, further comprising signaling means to inform the user that the heating means is at the selected temperature.

8. The apparatus in accordance with claim 7, further comprising means to select one or more additional temperatures, so that, when cyclical operation is selected, heat will be alternately be applied first at the first selected temperature, then at the second selected temperature, and so on until all the selected temperatures have been applied in sequence, then at first selected temperature, and repeating indefinitely.

9. The apparatus in accordance with claim 8, further comprising a grid at the contact end, said grip having a multiplicity of apertures, whereby the heat transfer surface contains a multiplicity of protrusions which extend through the grid apertures when the surface is in extended position.

10. The apparatus in accordance with claim 1, further comprising an essentially spherical heat transfer surface filled with liquid of a high specific heat, and wherein the temperature detection means and heating means are located within said liquid.

11. The apparatus in accordance with claim 10, further comprising means to select one of a multiplicity of temperatures, each such temperature comprising a best effective temperature for a particular treatment, and comprising means to control skin temperature to within one-half degree centigrade.

12. The apparatus according to claim 1, wherein the heating means further comprises an heat source recessed within said contact end, wherein the contact end is enclosed by a grip having a multiplicity of apertures allowing heating of the skin by said indirect means, and wherein said temperature detection means are located in proximity to the grid.

13. The apparatus according to claim 12, wherein said selection means provides a periodic heating of the skin, and wherein the selection means provides control of frequency and duty cycle of said heating.

14. A method for treating an itch or rash skin disease, comprising the following steps, in order:

selecting a temperature based on the type of a specific treatment;

raising the temperature of the diseased area to the selected temperature to a certain precision;

and maintaining the temperature of the diseased area for a desired time.

* * * * *